United States Patent
Ross et al.

(10) Patent No.: US 10,380,866 B1
(45) Date of Patent: Aug. 13, 2019

(54) DUAL CASE SYSTEM FOR FALL DETECTION DEVICE

(71) Applicant: MedHab, LLC, Mansfield, TX (US)

(72) Inventors: Johnny Ross, Mansfield, TX (US); James Olinger, Crowley, TX (US)

(73) Assignee: Med Hab, LLC., Mansfield, TX (US)

( * ) Notice: Subject to any disclaimer, the term of this patent is extended or adjusted under 35 U.S.C. 154(b) by 0 days.

(21) Appl. No.: 16/137,842

(22) Filed: Sep. 21, 2018

(51) Int. Cl.
*G08B 1/08* (2006.01)
*G08B 21/04* (2006.01)
*A44C 5/00* (2006.01)
*A61B 5/11* (2006.01)

(52) U.S. Cl.
CPC ........ *G08B 21/0446* (2013.01); *A44C 5/0053* (2013.01); *A61B 5/1117* (2013.01); *G08B 21/043* (2013.01)

(58) Field of Classification Search
CPC .................................. A61B 1/00; H04W 4/00
See application file for complete search history.

(56) References Cited

U.S. PATENT DOCUMENTS

| | | | |
|---|---|---|---|
| 8,615,377 B1 | 12/2013 | Yuen et al. | |
| 8,734,296 B1 | 5/2014 | Brumback et al. | |
| D706,531 S | 6/2014 | Park et al. | |
| D707,041 S | 6/2014 | Park et al. | |
| 8,747,336 B2 * | 6/2014 | Tran .................... | G06F 19/3418 600/587 |
| 8,762,101 B2 | 6/2014 | Yuen et al. | |
| 8,762,102 B2 | 6/2014 | Yuen et al. | |
| 8,784,271 B2 | 7/2014 | Brumback et al. | |
| 8,793,101 B2 | 7/2014 | Yuen et al. | |
| D714,672 S | 10/2014 | Park et al. | |
| D715,666 S | 10/2014 | Park et al. | |
| D717,680 S | 11/2014 | Park et al. | |
| 8,892,401 B2 | 11/2014 | Yuen et al. | |
| 8,909,543 B2 | 12/2014 | Tropper et al. | |
| 8,920,332 B2 | 12/2014 | Hong et al. | |
| 8,924,249 B2 | 12/2014 | Tropper et al. | |
| D720,635 S | 1/2015 | Park et al. | |
| 8,935,119 B2 | 1/2015 | Yuen | |
| 8,944,958 B1 | 2/2015 | Brumback et al. | |
| 8,945,017 B2 | 2/2015 | Venkatraman et al. | |
| 8,948,832 B2 | 2/2015 | Hong et al. | |
| 8,954,135 B2 | 2/2015 | Yuen et al. | |
| 8,956,303 B2 | 2/2015 | Hong et al. | |
| D727,183 S | 4/2015 | Park et al. | |
| D727,759 S | 4/2015 | Martinez et al. | |
| 8,998,815 B2 | 4/2015 | Venkatraman et al. | |
| 9,005,129 B2 | 4/2015 | Venkatraman et al. | |
| 9,026,927 B2 | 5/2015 | Brumback et al. | |
| 9,113,794 B2 | 8/2015 | Hong et al. | |

(Continued)

*Primary Examiner* — Shirley Lu
(74) *Attorney, Agent, or Firm* — Eric Karich; Karich & Associates (57) ABSTRACT

A dual case system includes a wrist band and a belt hook for operatively mounting a fall detection device on a user. The wrist band includes a central housing that is shaped to receive and frictionally engage the fall detection device. The clothing clip includes a main housing having an inner cavity which can be accessed through an upper perimeter for receiving and frictionally engaging the fall detection device. A hook extends from the main housing for removably mounting the main housing on the article of clothing of the user.

2 Claims, 5 Drawing Sheets

(56) References Cited

U.S. PATENT DOCUMENTS

| | | |
|---|---|---|
| 9,113,795 B2 | 8/2015 | Hong et al. |
| 9,237,855 B2 | 1/2016 | Hong et al. |
| D749,002 S | 2/2016 | Park et al. |
| 9,307,917 B2 | 4/2016 | Hong et al. |
| D759,516 S | 6/2016 | Ling et al. |
| D759,826 S | 6/2016 | Martinez et al. |
| D763,719 S | 8/2016 | Nielsen et al. |
| D766,758 S | 9/2016 | Park et al. |
| D768,028 S | 10/2016 | Ling et al. |
| 9,456,787 B2 | 10/2016 | Venkatraman et al. |
| D777,590 S | 1/2017 | Nielsen et al. |
| 9,655,548 B2 | 5/2017 | Hong et al. |
| D790,374 S | 6/2017 | Lean et al. |
| D790,994 S | 7/2017 | Nielsen et al. |
| 9,728,059 B2 | 8/2017 | Arnold et al. |
| D796,368 S | 9/2017 | Lowe et al. |
| D800,596 S | 10/2017 | Ling et al. |
| 9,801,547 B2 | 10/2017 | Yuen et al. |
| D802,452 S | 11/2017 | Paschke et al. |
| D802,453 S | 11/2017 | Page et al. |
| D802,454 S | 11/2017 | Paschke et al. |
| D803,077 S | 11/2017 | Paschke et al. |
| 9,808,185 B2 | 11/2017 | Arnold et al. |
| D804,334 S | 12/2017 | Becker et al. |
| D805,418 S | 12/2017 | Lowe et al. |
| 9,851,808 B2 | 12/2017 | Yuen et al. |
| D806,599 S | 1/2018 | Nielsen et al. |
| D807,219 S | 1/2018 | Ling et al. |
| 9,880,157 B2 | 1/2018 | Levak et al. |
| D809,955 S | 2/2018 | Ling et al. |
| 9,891,717 B2 | 2/2018 | Pantelopoulos et al. |
| D813,695 S | 3/2018 | Nielsen et al. |
| D817,920 S | 5/2018 | Paschke et al. |
| D821,245 S | 6/2018 | Lowe et al. |
| D821,247 S | 6/2018 | Lean et al. |
| D822,526 S | 7/2018 | Lean et al. |
| 10,010,750 B2 | 7/2018 | Tropper et al. |
| 2018/0000385 A1* | 1/2018 | Heaton ............... G08B 29/186 |

\* cited by examiner

DUAL CASE SYSTEM FOR FALL DETECTION DEVICE

BACKGROUND OF THE INVENTION

Field of the Invention

This invention relates generally to fall detection devices, and more particularly to a dual case system for a fall detection device.

Description of Related Art

Hong, U.S. 2014/0378786, teaches a biometric monitoring device ("BMD") that is adapted to be worn around the wrist (via a wrist-band), or arm (via an arm-band). The BMD functions in multiple device modes depending on operational conditions of the devices, e.g., motion intensity, device placement, and/or activity type. The device modes are associated with various data processing algorithms. In some embodiments, the BMD is implemented as a wrist-worn or arm-worn device. The BMD determines that the user is engaged in a particular activity type by detecting a signature signal selectively associated with the particular activity type, and quantifies a physiological metric for the particular activity type.

Park, U.S. Pat. No. 9,600,994, teaches a device that is similar to the device disclosed in Hong, but which also may alternatively be mounted in a belt-clip. The device includes one or more motion sensors for sensing motion of the device and providing activity data indicative of the sensed motion. The device also includes one or more processors for monitoring the activity data, and receiving or generating annotation data for annotating the activity data with one or more markers or indicators to define one or more characteristics of an activity session.

Russell, U.S. Pat. No. 9,691,253, teaches a remote physiological monitoring device for monitoring a patient that is at-risk for falling. The system tracks movement data of a patient from one or more sensors. The device may be attached to the user's wrist, arm, thigh, or elsewhere via an article of clothing. Once it is determined that the at-risk condition is satisfied, the methods may also include issuing an alert based, at least in part, on the determination that the at-risk condition is satisfied.

Other similar devices are shown in Carlton-Foss, U.S. Pat. No. 8,217,795, Sweeney, U.S. Pat. No. 8,933,801, and Venkatraman, U.S. Pat. No. 9,456,787.

SUMMARY OF THE INVENTION

The present invention teaches certain benefits in construction and use which give rise to the objectives described below.

The present invention provides a dual case system for operatively mounting a fall detection device on a user, either around a wrist of the user, or to an article of clothing of the user. The dual case system includes a wrist band and a clothing clip. The wrist band includes a central housing having a top wall and opposing side walls and opposing end walls, the side walls and the end walls extending downwardly from the top surface to an opening perimeter, the top wall, the side walls, and the end walls together forming a receiving cavity which can be accessed through the opening perimeter, the receiving cavity being shaped to receive and frictionally engage the fall detection device; a first attachment strap extending from one of the end walls of the central housing; and a second attachment strap extending from the other of the end walls of the central housing for removably engaging the first attachment strap for securing the wrist band around the user's wrist.

In one embodiment, the clothing clip includes a main housing having a base, a front wall, a rear wall, and lateral walls, the front wall, the rear wall, and the lateral walls extending upwardly from the base to an upper perimeter, the base, the front and rear walls, and the lateral walls together forming an inner cavity which can be accessed through the upper perimeter, the inner cavity being shaped to receive and frictionally engage the fall detection device; a cutout window formed in part of the front wall and part of the base, the cutout window enabling the user to push the fall detection device from within the inner cavity; and a hook extending from the main housing for removably mounting the main housing on the article of clothing of the user.

A primary objective of the present invention is to provide a dual case system having advantages not taught by the prior art.

Another objective is to provide a dual case system that enables a user to mount a fall detection device in various locations on his or her body.

Another objective is to provide a dual case system that includes a superior wrist band construction that is easy for elderly patients to use, and which does not interfere with their everyday activities, but which is still accurate in detecting falls.

Another objective is to provide a dual case system that includes a superior clothing clip construction that is easy for elderly patients to use, and which does not interfere with their everyday activities, but which is still accurate in detecting falls.

A further objective is to provide a dual case system that is easy and flexible to use, and still accurate in determining if a fall has occurred.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention. In such drawings.

DETAILED DESCRIPTION OF THE INVENTION

The above-described drawing figures illustrate the invention, a dual case system for operatively mounting a fall detection device on a person.

Figure 1:
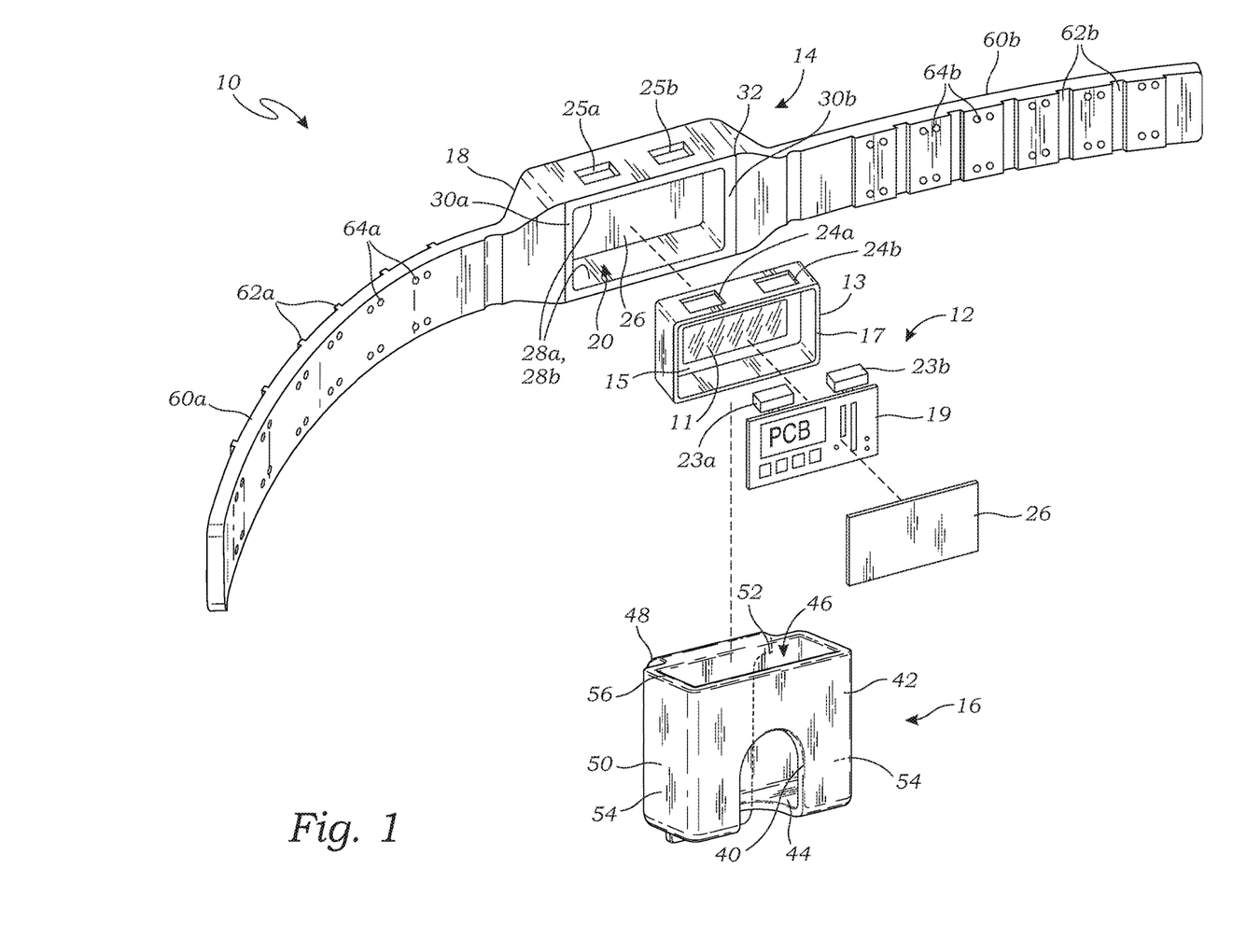
FIG. 1 is an exploded perspective view of a dual case system according to one embodiment of the present invention, illustrating both a wrist band and a clothing clip which may be alternatively used to operably wear a fall detection device.

FIG. 1 is an exploded perspective view of one embodiment of a dual case system 10 of the present invention, illustrating both a wrist band 14 and a clothing clip 16 which may be alternately used to wear a fall detection device 12. The wrist band 14 and the clothing clip 16 each includes a means for engaging the fall detection device 12, so that a user may easily switch the fall detection device 12 between these two different options. Further forms of such housings may also be included in alternative embodiments, and this application should not be limited to these particular embodiments.

The fall detection device 12 may operate in communication with other electronic devices to track movements of the user, detect if the user has fallen, or been injured, or requires assistance. The user is monitored by such a wearable sensor device for the purpose of detecting falls and other traumatic events that may require urgent medical care. The device 12 is equipped with detection software that is capable of determining a fall regardless of where on the person the sensor is mounted.

As shown in FIG. 1, the fall detection device 12 includes a device housing 13 that defines a device cavity 15 that is sized and shaped to receive a circuit board 19 and any associated electronics (e.g., memory, processor, accelerometers, batteries, etc.). Since the construction of a fall detection device 12 is known in the art, it is not described in greater detail herein. The device housing 13 extends to a device perimeter 17, and a device cover 21 is shaped to fit over the device perimeter 17 for covering the device cavity 15 for holding the circuit board 19 within the device cavity 15.

As shown in FIG. 1, the device cover 21 may be in the form of a rigid plate, as illustrated, or in another form for closing the cavity 15 and securing and protecting the electronics. In this embodiment, the cover 21 may be welded to the perimeter 17, although other fastening methods may also be used (e.g., mechanical fasteners or coupling mechanisms, adhesives, etc.).

In one embodiment, an adhesive pad 11 may be provided in the bottom of the device cavity 15, which bonds to the circuit board 19 during assembly and holds the circuit board 19 in place. In alternative embodiments, other forms of adhesives, putties, mechanical fasteners, or other suitable materials may also be used. In yet another embodiment, the circuit board 19 is not fastened in place.

In the embodiment of FIG. 1, the circuit board 19 further includes buttons 23a and 23b which enable one form of control over the fall detection device 12. In this embodiment, there are two buttons 23a and 23b, but there may be a greater or fewer number of buttons in other embodiments. In this embodiment, pressing the first button 23a activates an alert that there has been a fall, while the second button 23b is used to indicate that there has been no fall, cancelling a false positive from the fall detection software. Both buttons 23a and 23b may be pressed together to indicate that emergency help is needed.

In the embodiment of FIG. 1, the first and second buttons 23a and 23b are made accessible to the user via first and second apertures 24a and 24b through the device housing 13. When the wrist band 14 is used, the buttons may be accessed through the first and second apertures 25a and 25b, which are discussed in greater detail below. When the clothing clip 16 is used, an entrance formed by an upper perimeter 56 enables access to the buttons, as discussed in greater detail below.

While this embodiment discusses the use of buttons, these are not required in some embodiments, which may use voice commands, or other methods known in the art for controlling the fall detection device 12.

Figure 2:
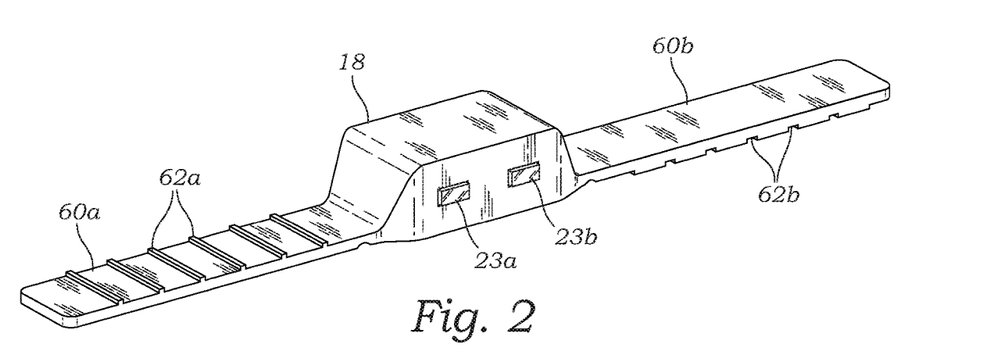
FIG. 2 is a top perspective view of the wrist band.
Figure 3:
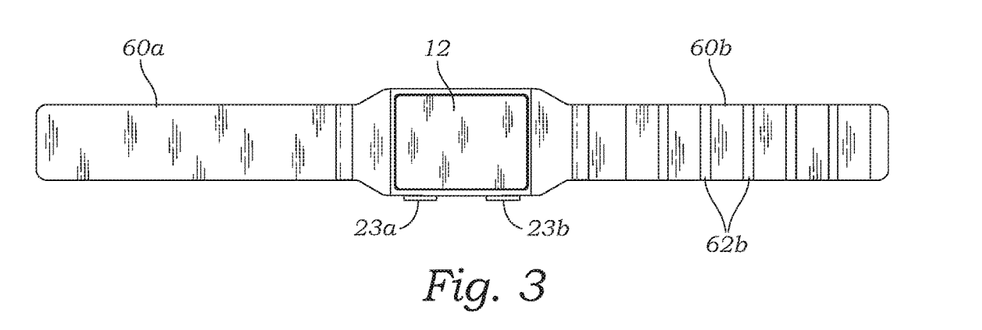
FIG. 3 is a bottom plan view of the wrist band.
Figure 4:
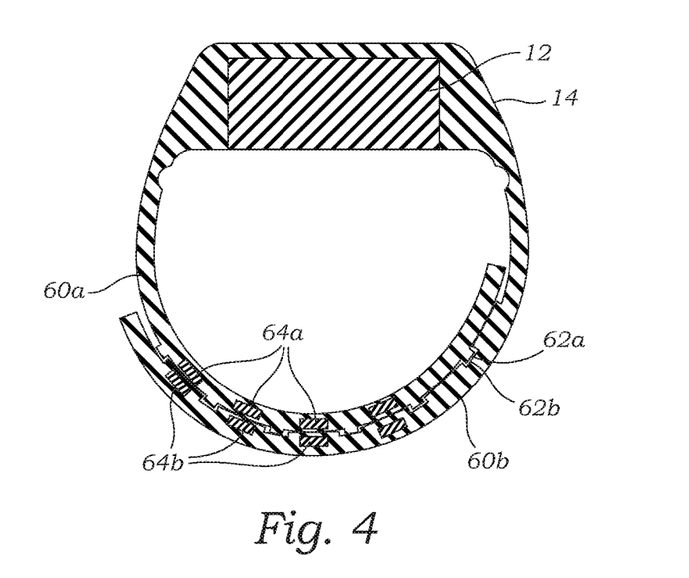
FIG. 4 is a side cross-sectional view of the wrist band illustrating the operation of the bands for fastening the wrist band closed.

FIG. 2 is a top perspective view of the wrist band 14, showing the central housing 18 for the fall detection device 12. FIG. 3 is a bottom plan view of the wrist band 14, showing the hollow receiving cavity 20. FIG. 4 is a side cross-sectional view of the wrist band 14, illustrating the operation of a first attachment strap 60a and a second attachment strap 60b for fastening the wrist band 14 closed.

The wrist band 14 includes a means for securing the wrist band 14 around the wrist (or ankle, or other part of a limb) of the user. In one embodiment, as shown in FIGS. 1-4, the first attachment strap 60a has longitudinally spaced lateral ridges 62a, and the second attachment strap 60b includes lateral slots shaped to receive and frictionally engage the lateral ridges 62a. In this embodiment, the first and second attachment straps 60a and 60b further include first and second sets of magnets 64a and 64b which are positioned so that they bias the first and second attachment straps 60a and 60b towards a locking configuration shown in FIG. 4, wherein the ridges 62a engage the slots 62b. The length may be adjusted, but the straps will naturally move towards one of the locking positions, and the ridges and slots will removably engage each other. When the user wants to remove the wrist band 14, he or she may simply separate the bands by overcoming the magnetic bias of the magnets 64a and 64b.

In this embodiment, the wrist band 14 includes a central housing 18 comprising a top wall 26, opposing side walls 28a and 28b, and opposing end walls 30a and 30b. The top wall 26 is resilient material that a user may press to disengage the fall detection device 12 from the receiving cavity 20. In this embodiment, the material is rubber or rubber-like, though any other pliable material (e.g. plastic, etc.) may be used to the same effect. The fall detection device 12 is inserted into the receiving cavity 20, which is shaped to receive and frictionally engage the device 12. The side walls and the end walls extending downwardly to the opening perimeter are planar and do not extend around the fall detection device.

The fall detection device 12 is held within the receiving cavity 20 by the wrist of the user when the wrist band 14 is worn. The receiving cavity 20 is a rectangular prism formed by the top wall 26, the side walls 28, and the end walls 30a and 30b together, and can be accessed through an opening perimeter 32, which is formed by the side walls 28 and end walls 30a and 30b extending downwardly from the top wall 26. The side walls 28 and the end walls 30a and 30b are planar and do not extend around the fall detection device (i.e., there is no lip that extends around the device 12).

As discussed above, in this embodiment the first side wall 28a has the first and second apertures 25a and 25b that are positioned to receive the first and second buttons 23a and 23b of the fall detection device 12. In this embodiment, there are two apertures 25a and 25b, though the number of apertures is dependent on the number of buttons and therefore may be greater or fewer in other embodiments. The central housing 18 may mimic the receiving cavity's 20 rectangular shape, and then extends to taper downward on either side, past the opening perimeter 32 and into two attachment straps 60a and 60b. In alternative embodiments, however, alternative shapes may be used, according to the needs of the product designer.

In this embodiment, the attachment straps 60a and 60b are connected to either end of the central housing 18, although in alternative embodiments they may be attached using other configurations known in the art.

Figure 5:
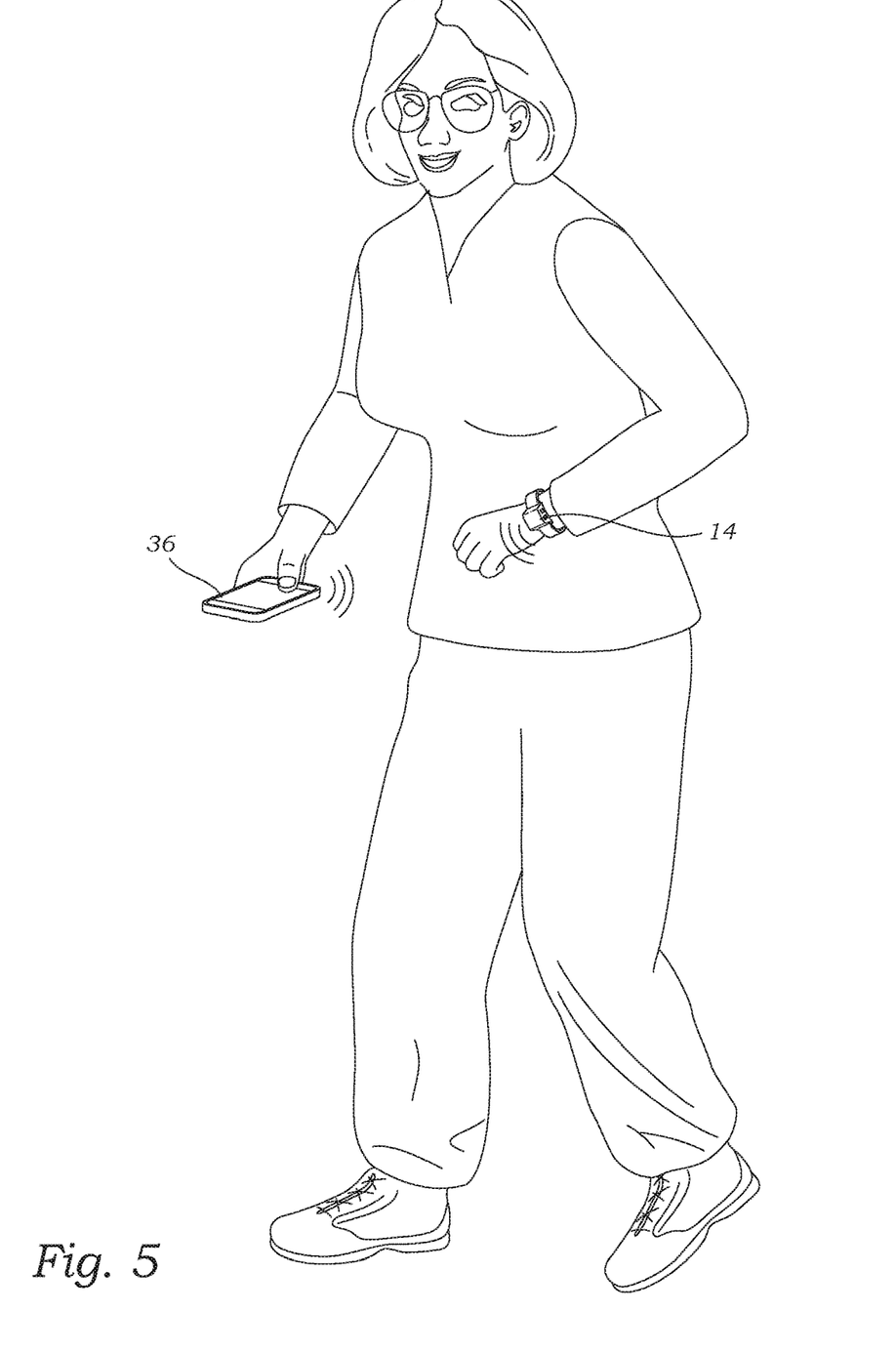
FIG. 5 is a perspective view of a person wearing the wrist band so that the fall detection device may communicate with a smart phone.

FIG. 5 is a perspective view of a person wearing the wrist band 14 so that the fall detection device 12 may communicate with a smart phone 36, though the fall detection device 12 may transmit data to other types of electronic devices (e.g., a laptop, etc.).

Figure 6:
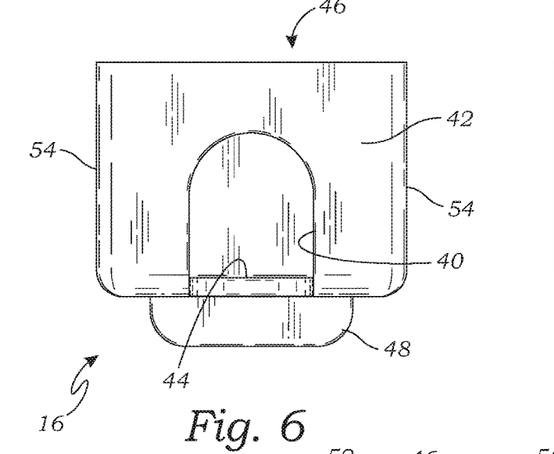
FIG. 6 is a front elevational view of the clothing clip.
Figure 7:
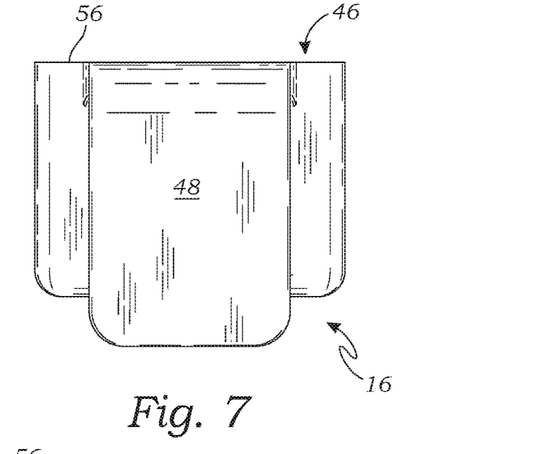
FIG. 7 is a rear elevational view of the clothing clip.
Figure 8:
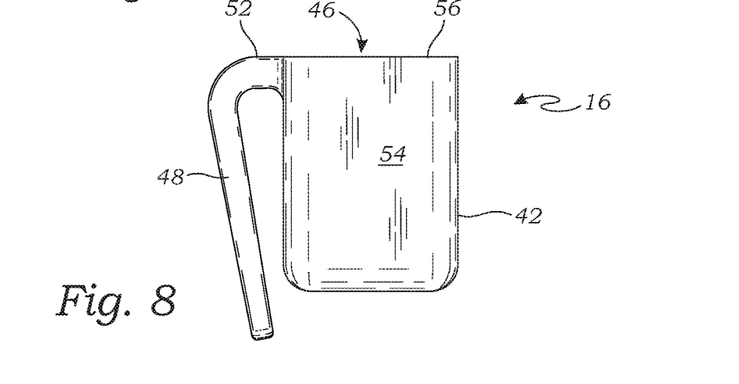
FIG. 8 is a side view of the clothing clip.
Figure 9:
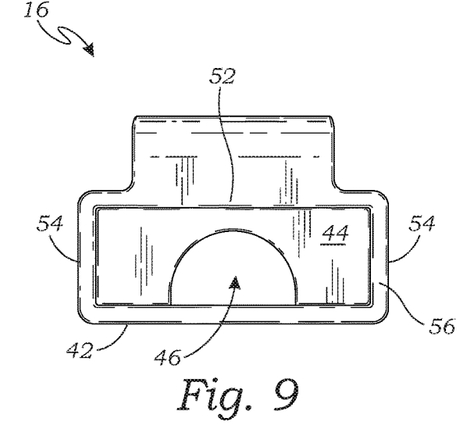
FIG. 9 is a top plan view of the clothing clip.
Figure 10:
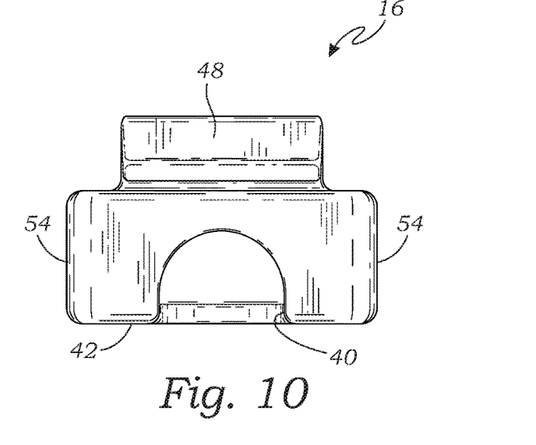
FIG. 10 is a bottom plan view of the clothing clip.

FIG. 6 is a front elevational view of the clothing clip 16, showing a cutout window 40 on the front wall 42 and the base 44 that enables a user to push the fall detection device 12 from within the inner cavity 46. FIG. 7 is a rear elevational view of the clothing clip 16, showing a hook 48 for removably mounting a main housing 50 on an article of clothing of the user. FIG. 8 is a side view of the clothing clip 16. FIG. 9 is a top plan view of the clothing clip 16. FIG. 10 is a bottom plan view of the clothing clip 16.

As shown in FIGS. 1 and 6-9, the main housing 50 of the clothing clip 16 includes a base 44, a front wall 42, a rear wall 52, and two lateral walls 54, all of which together form an inner cavity 46. The base 44 and the front wall 42 are molded to form the cutout window 40, which is approximately the width of a human finger and extends, in this embodiment, without interruption 50-95% up the front wall 42, and also somewhat into the base 44. The cutout window 40 may be oval, rectangular, or other suitable shape to enable the user to insert his or her finger through the window. The cutout window 40 allows access into the inner cavity 46, enabling the user to push the fall detection device 12 out of the inner cavity. The inner cavity is shaped to receive and may frictionally engage the fall detection device 12, and is formed by the base 44, the front wall 42, the rear wall 52, and the lateral walls 54 together. The fall detection device 12 can be inserted into the inner cavity 46 through an entrance at the upper perimeter 56. The upper perimeter 56 is formed by the front wall 42, the rear wall 52, and the lateral walls 54 extending upwardly from the base 44.

Attached to the upper perimeter 56 is the hook 48, which extends from the rear wall 52 for securing the clothing clip 16 onto a user's desired article of clothing. In some instances, the clothing clip 16 may be clipped onto a belt, bra, or other article of clothing for holding the In this embodiment, the clothing clip 16 is made of rigid plastic, though it may be constructed of other suitable materials known in the art.

Figure 11:
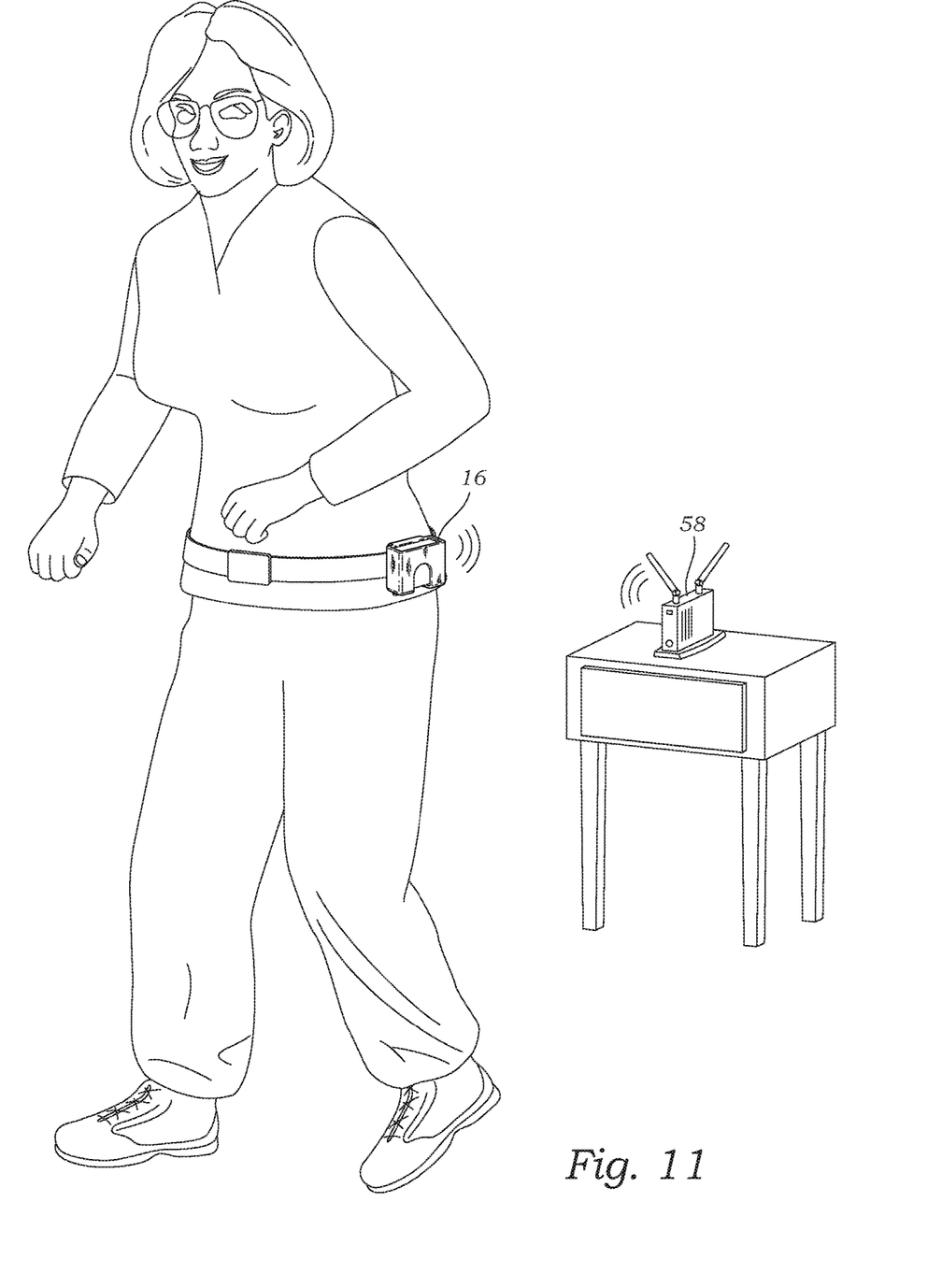
FIG. 11 is a perspective view of the person wearing the clothing clip so that the fall detection device may communicate with a network hub.

FIG. 11 is a perspective view of the person wearing the clothing clip 16 so that the fall detection device 12 may communicate with a network hub 58, though the fall detection device 12 may transmit data to other types of electronic devices (e.g., a laptop, etc.).

As used in this application, the words "a," "an," and "one" are defined to include one or more of the referenced item unless specifically stated otherwise. The terms "approximately" and "about" are defined to mean +/−10%, unless otherwise stated. Also, the terms "have," "include," "contain," and similar terms are defined to mean "comprising" unless specifically stated otherwise. Furthermore, the terminology used in the specification provided above is hereby defined to include similar and/or equivalent terms, and/or alternative embodiments that would be considered obvious to one skilled in the art given the teachings of the present patent application. While the invention has been described with reference to at least one particular embodiment, it is to be clearly understood that the invention is not limited to these embodiments, but rather the scope of the invention is defined by claims made to the invention.

What is claimed is:

1. A dual case system for operatively mounting a fall detection device on a user, either around a wrist of the user, or to an article of clothing of the user, the dual case system comprising:
   a wrist band comprising:
      a central housing having a top wall and opposing side walls and opposing end walls, the side walls and the end walls extending downwardly from the top surface to an opening perimeter, the top wall, the side walls, and the end walls together forming a receiving cavity which can be accessed through the opening perimeter, the receiving cavity being shaped to receive and frictionally engage the fall detection device;
      a first attachment strap extending from one of the end walls of the central housing;
      a second attachment strap extending from the other of the end walls of the central housing; and
      a plurality of longitudinally spaced lateral ridges on the first attachment strap, a plurality of grooves on the second attachment strap, a first set of magnets disposed in the first attachment strap, and a second set of magnets disposed in the second attachment strap, the first and second sets of magnets being positioned to magnetically bias the first and second attachment straps towards a locking configuration wherein the ridges engage the slots; and
   a clothing clip comprising:
      a main housing having a base, a front wall, a rear wall, and lateral walls, the front wall, the rear wall, and the lateral walls extending upwardly from the base to an upper perimeter, the base, the front and rear walls, and the lateral walls together forming an inner cavity which can be accessed through the upper perimeter, the inner cavity being shaped to receive and frictionally engage the fall detection device;
      a cutout window formed in part of the front wall and part of the base, the cutout window enabling the user to push the fall detection device from within the inner cavity; and
      a hook extending from the main housing for removably mounting the main housing on the article of clothing of the user.

2. A dual case system for detecting a fall of a user, the dual case system comprising:
   a fall detection device for detecting a fall;
   a wrist band comprising:
      a central housing having a top wall and opposing side walls and opposing end walls, the side walls and the end walls extending downwardly from the top surface to an opening perimeter, the top wall, the side walls, and the end walls together forming a receiving cavity which can be accessed through the opening perimeter, the receiving cavity being shaped to receive the fall detection device;
      a first attachment strap extending from one of the end walls of the central housing;
      a second attachment strap extending from the other of the end walls of the central housing; and a plurality of longitudinally spaced lateral ridges on the first attachment strap, a plurality of grooves on the second attachment strap, a first set of magnets disposed in the first attachment strap, and a second set of magnets disposed in the second attachment strap, the first and second sets of magnets being positioned to magnetically bias the first and second attachment straps towards a locking configuration wherein the ridges engage the slots; and a clothing clip comprising:
- a main housing having a base, a front wall, a rear wall, and lateral walls, the front wall, the rear wall, and the lateral walls extending upwardly from the base to an upper perimeter, the base, the front and rear walls, and the lateral walls together forming an inner cavity which can be accessed through the upper perimeter, the inner cavity being shaped to receive and frictionally engage the fall detection device;
- a cutout window formed in part of the front wall and part of the base, the cutout window enabling the user to push the fall detection device from within the inner cavity; and
- a hook extending from the main housing for removably mounting the main housing on the article of clothing of the user.

* * * * *